(12) United States Patent
Fujikane et al.

(10) Patent No.: US 9,855,356 B2
(45) Date of Patent: Jan. 2, 2018

(54) LIQUID TREATMENT METHOD AND LIQUID TREATMENT APPARATUS FOR TREATING A LIQUID WITH PLASMA

(71) Applicant: Panasonic Intellectual Property Management Co., Ltd., Osaka (JP)

(72) Inventors: Masaki Fujikane, Osaka (JP); Mari Onodera, Osaka (JP); Yuka Okada, Hyogo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 70 days.

(21) Appl. No.: 15/141,590

(22) Filed: Apr. 28, 2016

(65) Prior Publication Data

US 2016/0339128 A1 Nov. 24, 2016

(30) Foreign Application Priority Data

May 18, 2015 (JP) .................. 2015-101319

(51) Int. Cl.
| | |
|---|---|
| *A61L 2/14* | (2006.01) |
| *G01N 27/36* | (2006.01) |
| *A61L 2/24* | (2006.01) |
| *G01N 27/30* | (2006.01) |
| *G01N 33/28* | (2006.01) |
| *C02F 1/00* | (2006.01) |
| *C02F 1/46* | (2006.01) |
| *C02F 1/66* | (2006.01) |

(52) U.S. Cl.
CPC .............. *A61L 2/14* (2013.01); *A61L 2/24* (2013.01); *C02F 1/008* (2013.01); *C02F 1/4608* (2013.01); *C02F 1/66* (2013.01); *G01N 33/28* (2013.01); *C02F 2209/06* (2013.01); *C02F 2303/04* (2013.01)

(58) Field of Classification Search
None
See application file for complete search history.

(56) References Cited

U.S. PATENT DOCUMENTS

| | | |
|---|---|---|
| 2009/0098062 A1 | 4/2009 | Bobbert |
| 2010/0126940 A1 | 5/2010 | Ryu et al. |
| 2012/0156093 A1 | 6/2012 | Kitano |
| 2014/0014516 A1 | 1/2014 | Kumagai et al. |

(Continued)

FOREIGN PATENT DOCUMENTS

| | | |
|---|---|---|
| EP | 2206521 | 7/2010 |
| JP | 2003-340454 | 12/2003 |
| JP | 2009-255027 | 11/2009 |

(Continued)

*Primary Examiner* — Kishor Mayekar
(74) *Attorney, Agent, or Firm* — McDermott Will & Emery LLP

(57) ABSTRACT

A liquid treatment method according to an aspect of the present disclosure comprises: starting application of a power between a pair of electrodes to generate plasma, which causes active species to be produced in a liquid; measuring the hydrogen ion concentration in the liquid while the plasma is generated; measuring a time elapsed after the starting the application of the power; and stopping the application of the power when a value calculated by (a) multiplying the hydrogen ion concentration by the elapsed time or (b) integrating the hydrogen ion concentration with respect to the elapsed time is larger than a first threshold.

4 Claims, 11 Drawing Sheets

(56) References Cited

U.S. PATENT DOCUMENTS

2015/0102255 A1    4/2015    Imai et al.

FOREIGN PATENT DOCUMENTS

| | | |
|---|---|---|
| JP | 2010-523326 | 7/2010 |
| JP | 2012-217917 | 11/2012 |
| JP | 2014-113517 | 6/2014 |
| WO | 2007/048808 | 5/2007 |
| WO | 2009/041049 | 4/2009 |
| WO | 2011/027542 | 3/2011 |
| WO | 2012/157248 | 11/2012 |
| WO | 2014/171138 | 10/2014 |

LIQUID TREATMENT METHOD AND LIQUID TREATMENT APPARATUS FOR TREATING A LIQUID WITH PLASMA

BACKGROUND

1. Technical Field

The present disclosure relates to a method and an apparatus for treating a liquid with plasma.

2. Description of the Related Art

Techniques in which plasma is used for purifying or sterilizing a liquid or a gas have been studied. For example, there has been disclosed a sterilizing apparatus that produces active species such as OH radicals by using plasma and sterilizes water by using the active species.

A sterilizing apparatus described in Japanese Unexamined Patent Application Publication No. 2009-255027 includes a pair of electrodes. Upon a negative high-voltage pulse (2 to 50 kV/cm, 100 Hz to 20 kHz) being applied between the pair of electrodes, electrical discharge occurs. The energy of the electrical discharge causes water to evaporate and vaporize with shock waves, thereby generating a bubble containing water vapor. The electrical discharge generates plasma in the bubble.

In the sterilization method described in Japanese Patent No. 4408957, plasma is generated in or near a liquid whose pH has been set to 4.8 or less, and radicals produced by the plasma are brought into contact with the liquid in order to kill bacteria that are present in the liquid or on the surface of the liquid.

In the sterilization method described in Japanese Patent No. 5305274, plasma is generated in the gas phase by using a plasma generation device, ions are produced in the gas phase by the plasma, and an electric field is applied to the ions such that electrophoresis of the ions toward the liquid occurs. The pH of the liquid is set to 4.8 or less.

SUMMARY

A liquid treatment method according to an aspect of the present disclosure comprises: starting application of a power between a pair of electrodes to generate plasma, which causes active species to be produced in a liquid; measuring the hydrogen ion concentration in the liquid while the plasma is generated; measuring a time elapsed after the starting the application of the power; and stopping the application of the power when a value calculated by (a) multiplying the hydrogen ion concentration by the elapsed time or (b) integrating the hydrogen ion concentration with respect to the elapsed time is larger than a first threshold.

It should be noted that comprehensive or specific embodiments may be implemented as a system, an apparatus, an integrated circuit, a computer program, a computer-readable storage medium such as a CD-ROM, or any selective combination thereof.

One non-limiting and exemplary embodiment provides a liquid treatment method in which whether generation of plasma is to be stopped or continued can be determined in accordance with the progress of sterilization.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1:
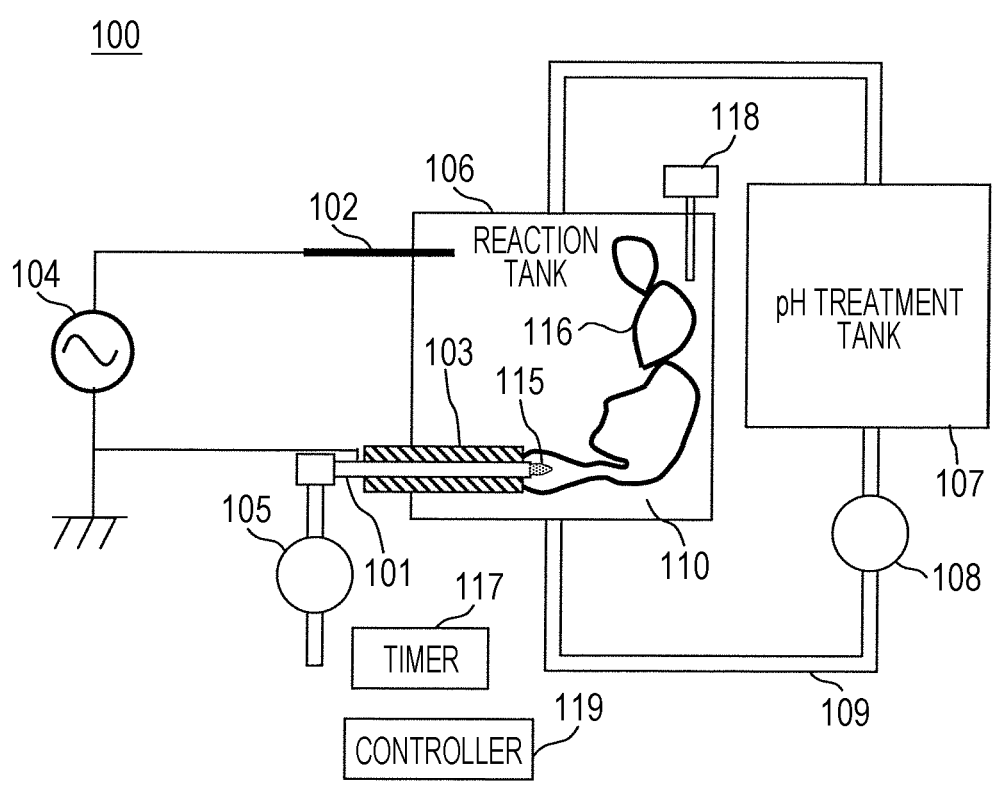
FIG. 1 is a block diagram illustrating an example of a liquid treatment apparatus according to an embodiment.

Underlying Knowledge Forming Basis of the Present Disclosure

The inventors found that the techniques, in which a plasma generation device is used for sterilizing a liquid, have the following issues.

The plasma generation device generates plasma to produce active species such as OH radicals, thereby sterilizing a liquid. However, typically, the progress of sterilization is determined by culturing the sterilized liquid for about 1 day and subsequently calculating the sterilization ratio or the number of the bacteria contained in the liquid. In other words, determining the sterilization ratio takes a considerable amount of time and effort in cultivation.

The inventors conducted a plurality of tests by changing the pH (abbreviation for "potential hydrogen" or "power of hydrogen") of a liquid to be sterilized and, as a result, found the following two points. Firstly, reducing the pH of the liquid to, for example, 7 or less markedly reduces the time required to sterilize the liquid by using plasma. Secondly, it is possible to estimate the sterilization ratio on the basis of a value calculated from the hydrogen ion concentration in the liquid and the time elapsed since discharge of plasma was started (hereinafter, referred to as "plasma-discharging time" or "elapsed time").

According to the first finding, controlling the pH of a liquid to be low may increase the sterilization efficiency. For example, it is known that, the larger the plasma-discharging time, the higher the hydrogen ion concentration in the liquid, even when the liquid is neutral. In other words, the larger the plasma-discharging time, the lower the pH of the liquid and the higher the sterilization efficiency. This is considered to be because, the higher the hydrogen ion concentration in the liquid (i.e., the lower the pH of the liquid), the larger the capability of active species such as OH radicals to attack bacteria.

According to the second finding, it is possible to readily determine the sterilization efficiency by estimating the sterilization ratio without consuming time and effort in cultivation. It is considered that the sterilization ratio can be estimated from the product of hydrogen ion concentration in a liquid to be sterilized and the plasma-discharging time on the basis of the Chick-Watson Law.

The Chick-Watson Law is briefly described below. According to the Chick-Watson Law, the sterilization efficacy of a disinfectant is represented as a function of the product of the concentration (C) of the disinfectant and the time (T) elapsed since the disinfectant was brought into contact with bacteria. The coefficient of the function varies depending on the combination of the disinfectant and bacteria. The Chick-Watson Law is represented by Expression 1 below.

$$C \cdot T = -(1/k)\log(N/N_0) \qquad (1)$$

In Expression 1, C represents the concentration of the disinfectant. In the case where plasma is used for sterilizing a liquid, active species such as OH radicals, which serve as particles that attack bacteria, are considered to correspond to the disinfectant. Although the hydrogen ion concentration is not the same as the concentration of the attacking particles, the hydrogen ion concentration is considered to have a correlation to C according to the first finding. Thus, in this embodiment, C is considered to be the hydrogen ion concentration. Therefore, the unit of C is the same as that (mol/L) of hydrogen ion concentration.

T represents the time elapsed since the attacking particles were brought into contact with bacteria. For example, T represents the plasma-discharging time. The unit of T is the minute.

$N_0$ represents the number of bacteria (cfu/ml) which is measured before the attacking particles are brought into contact with the bacteria (e.g., before discharge of plasma is started). The abbreviation "cfu", which stands for "colony forming unit", is the unit of the amount of bacteria, that is, the number of units capable of forming a colony.

N represents the number of bacteria (cfu/ml) which is measured at the time T elapsed since the attacking particles were brought into contact with the bacteria (e.g., at the plasma-discharging time T).

In Expression 1, k represents a killing efficacy coefficient. The unit of k is (mol/L)·min. The killing efficacy coefficient varies depending on the type of disinfectant and the type of bacteria.

The left-hand side of Expression 1, that is, the product $C \cdot T$ of the hydrogen ion concentration C and the plasma-discharging time T, is considered to represent the amount of work done by the active species, such as OH radicals, attacking bacteria as attacking particles. The right-hand side of Expression 1, that is, $N/N_0$, represents the proportion of the number of bacteria that remain at the plasma-discharging time T. The sterilization ratio is represented by $1-(N/N_0)$.

It is considered that the sterilization ratio can be estimated on the basis of the product of the hydrogen ion concentration in a liquid to be sterilized and the plasma-discharging time or an integral of the hydrogen ion concentration in the liquid with respect to the plasma-discharging time.

Overview of Embodiments

In one general aspect, the techniques disclosed here feature a liquid treatment method in which a plasma generation device including a pair of electrodes and a power supply that applies a power between the pair of electrodes is used. The liquid treatment method includes preparing a liquid to be sterilized; applying a power between the pair of electrodes by using the power supply in order to generate plasma from the plasma generation device, and thereby producing active species in the liquid; measuring the hydrogen ion concentration in the liquid while the plasma is generated; measuring the time elapsed since the power supply started the application of the power while the plasma is generated; stopping the power supply from applying the power when the product of the hydrogen ion concentration and the elapsed time is larger than a first threshold, and allowing the power supply to continue applying the power when the product is equal to or smaller than the first threshold. The liquid treatment method may address the issue of time and effort required to determine the sterilization ratio by cultivation.

In this method, it is possible to determine whether the application of the power is to be continued or stopped in accordance with the sterilization ratio. That is, it is possible to determine whether generation of plasma is to be continued or stopped. The first threshold may be set in accordance with a desired sterilization ratio. This method also reduces time and effort required to determine the progress of sterilization by cultivation.

The liquid treatment method may further include adding an acidic substance to the liquid when the above-described product is smaller than a second threshold at the time the elapsed time has reached a predetermined time. The second threshold may be equal to or smaller than the first threshold.

In such a case, when the sterilization effect is smaller than the expected one at the time a predetermined amount of time has elapsed, the pH of the liquid is reduced by adding an acidic substance to the liquid. This increases the sterilization effect and reduces the time required for sterilization to be within a desired range.

The second threshold may be equal to or smaller than the first threshold. The predetermined time may be the time the above-described product is empirically considered to reach the second threshold. In the case where the liquid treatment method is applied to a washing machine, the acidic substance may be an acidic detergent.

The first threshold may be $1 \times 10^{-3}$ min·mol/L.

In such a case, discharge of plasma may be stopped at the time the number of bacteria reaches less than one hundredth of the initial number of bacteria.

In another general aspect, the techniques disclosed here feature a liquid treatment apparatus including a plasma generation device including a pair of electrodes and a power supply that applies a power between the pair of electrodes, the plasma generation device applying a power between the electrodes by using the power supply in order to generate plasma and thereby producing active species in a liquid; a sensor that measures the hydrogen ion concentration in the liquid while the plasma generation device generates plasma; a timer that measures the time elapsed since the power supply started applying the power between the electrodes; and a controller that stops the power supply from applying the power between the electrodes when the product of the hydrogen ion concentration measured by the sensor and the elapsed time measured by the timer is larger than the first threshold.

In another general aspect, the techniques disclosed here feature a washing machine including the above-described liquid treatment apparatus.

The above-described general or specific embodiments may be implemented as an apparatus for purifying water for drinking or a hot-water tank apparatus included in washing toilet seats.

Hereinafter, embodiments are described specifically with reference to the attached drawings.

The following embodiments are all comprehensive or specific examples. All numbers, shapes, materials, components, arrangement of the components, connection between the components, steps, and order of the steps described in the following embodiments are merely an example and are not intended to limit the scope of the present disclosure. Among the components described in the following embodiments, components that are not described in the independent claims are described as an optional component.

The expression "sterilization is completed" used herein means that the number of bacteria has been reduced to less than one hundredth of the initial number of bacteria.

Embodiments

[1. Structure of Liquid Treatment Apparatus]

FIG. 1 is a block diagram illustrating an example of a liquid treatment apparatus 100 according to an embodiment. The liquid treatment apparatus 100 may be used as a water purification apparatus for producing drinking water, a washing machine, and a hot-water tank apparatus included in washing toilet seats, for example. As illustrated in FIG. 1, the liquid treatment apparatus 100 includes a first metal electrode 101, a second metal electrode 102, an insulator 103, a power supply 104, a feed pump 105, a reaction tank 106, a pH treatment tank 107, a circulation pump 108, a pipe 109, a timer 117, a pH meter 118, and a controller 119.

The first metal electrode 101 is, for example, a rod-like electrode attached to the reaction tank 106 such that at least a portion of the first metal electrode 101 is exposed inside the reaction tank 106.

The second metal electrode 102 is, for example, a rod-like electrode attached to the reaction tank 106 such that at least a portion of the second metal electrode 102 is exposed inside the reaction tank 106.

The insulator 103 is arranged to cover the outer periphery of the first metal electrode 101. A ventilation gap is left between the inner periphery of the insulator 103 and the outer periphery of the first metal electrode 101. The gap is, for example, located in the vicinity of the ends of the insulator 103 and the first metal electrode 101. The insulator 103 is attached to an opening of the reaction tank 106. The gap communicates with a space inside the reaction tank 106.

The power supply 104 applies a power between the pair of electrodes, that is, the first metal electrode 101 and the second metal electrode 102 in order to generate plasma 115 and thereby produces active species such as OH radicals in a liquid 110 to be treated.

For applying a power between the pair of electrodes, the power supply 104 applies, for example, a pulse voltage or an alternating voltage between the first metal electrode 101 and the second metal electrode 102. For example, a negative high-voltage pulse of 2 to 50 kV/cm and 1 Hz to 100 kHz is applied. The waveform of the voltage may be a pulse-like waveform, a half-sine waveform, or a sine waveform. The amount of current that flows between the pair of electrodes is, for example, 1 mA to 3 A. Specifically, the power supply 104 applies a pulse voltage having a peak voltage of 4 kV, a pulse width of 1 μs, and a frequency of 30 kHz between the first metal electrode 101 and the second metal electrode 102. The input power of the power supply 104 is, for example, 30 W. In the case where a pulse voltage having a certain frequency is continuously applied between the pair of electrodes, a time during which the voltage is 0 V may be present per period of the waveform of the pulse voltage. In this embodiment, it is considered that application of the power is not stopped but continued during such a time.

The feed pump 105 feeds a gas into the gap between the first metal electrode 101 and the insulator 103 and forms a bubble 116 at the ends of the insulator 103 and the first metal electrode 101 in a continuous manner. Although it is possible to generate the plasma 115 between the pair of electrodes without forming the bubble 116, the presence of the bubble 116 increases the efficiency with which the plasma 115 produces the active species.

The reaction tank 106 stores liquid 110. The liquid 110 is an example of the liquid to be treated and/or sterilized.

The pH treatment tank 107 stores the liquid 110, for example. The pH treatment tank 107 may not be provided in the case where the liquid treatment apparatus 100 is used as a water purification apparatus for producing drinking water, or a hot-water tank apparatus included in washing toilet seats, for example. In the case where the liquid treatment apparatus 100 is used as a washing machine, the pH treatment tank 107 may serve as a washing tank for washing and dewatering, and the reaction tank 106 may serve as a subtank for sterilization.

The circulation pump 108 causes the liquid 110 to circulate between the reaction tank 106 and the pH treatment tank 107 through the pipe 109.

The pipe 109 is a pipe with which the reaction tank 106, the pH treatment tank 107, and the circulation pump 108 are connected to one another.

The timer 117 measures the time elapsed since the power supply 104 started applying a power to the pair of electrodes. If the entirety or a part of the liquid 110 is replaced, the timer 117 may measure the time elapsed since the replacement of the liquid 110 was done.

The pH meter 118 is a sensor that measures the hydrogen ion concentration in the liquid 110 to be sterilized. The pH meter 118 includes, for example, glass electrodes and a semiconductor chip.

The controller 119 controls the operation of the liquid treatment apparatus 100. During the sterilization treatment, for example, when the product of the hydrogen ion concentration in the liquid 110 and the elapsed time is larger than a first threshold, the controller 119 stops the power supply 104 from applying a power between the electrodes. Otherwise, that is, when the above product is equal to or smaller than the first threshold, the controller 119 allows the power supply 104 to continue applying a power between the electrodes. The first threshold may be set to, for example, $1 \times 10^{-3}$ min·mol/L in order to complete sterilization of the liquid 110.

[2. Operation of Liquid Treatment Apparatus]

An operation of the above-described liquid treatment apparatus 100 in a sterilization treatment is described below.

Figure 2:
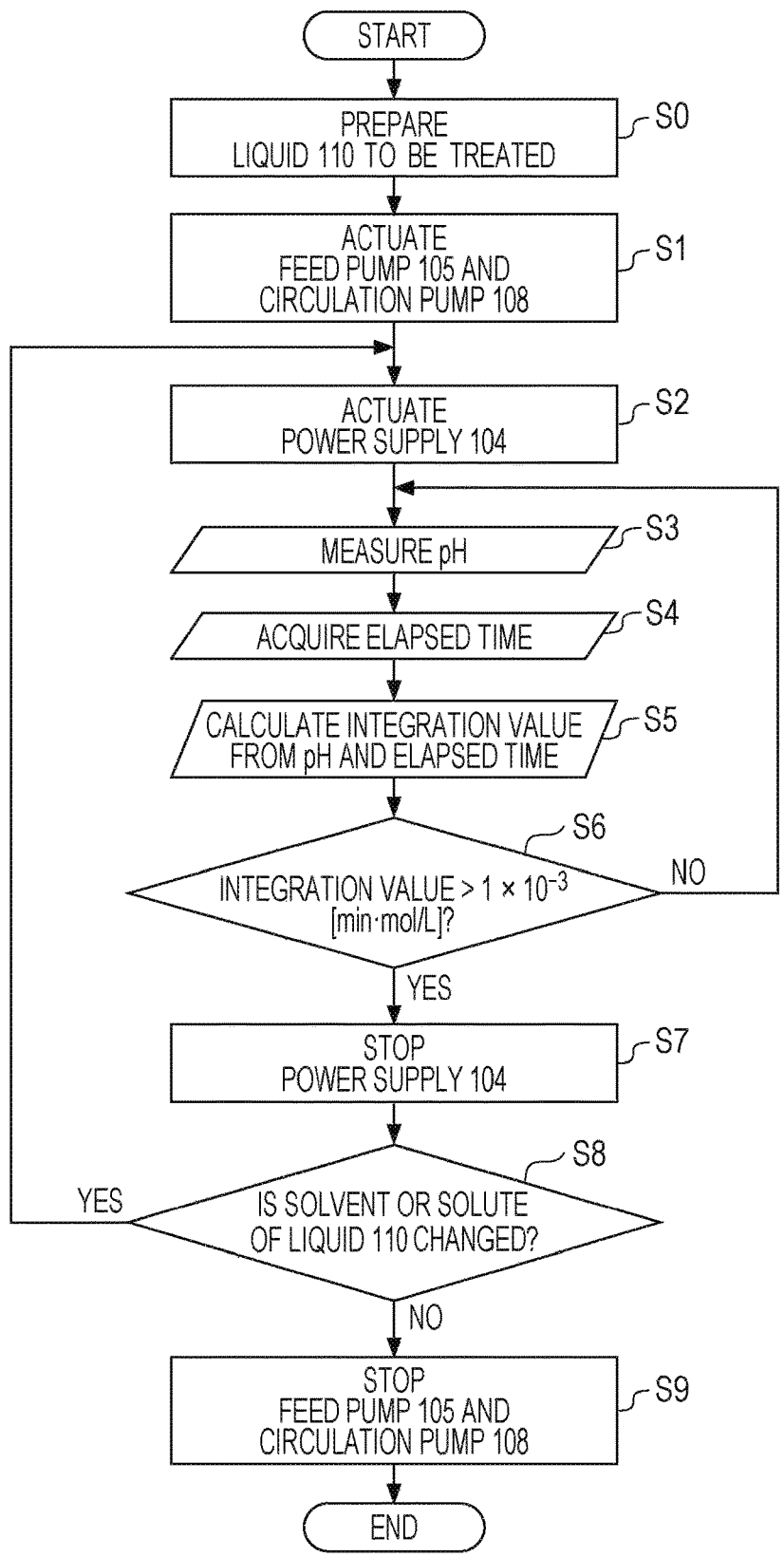
FIG. 2 is a flowchart illustrating an example of a liquid treatment method according to an embodiment.

FIG. 2 is a flowchart illustrating an example of a liquid treatment method according to an embodiment. A liquid that is to be sterilized is prepared. Specifically, a liquid 110 to be treated is stored in the reaction tank 106 and the pH treatment tank 107 (Step S0). For example, in the case where the liquid treatment apparatus 100 is used as a washing machine, water is poured into a washing tub containing clothes, that is, the pH treatment tank 107, and a detergent is charged into the washing tub. The detergent may be, for example, an acidic detergent.

The controller 119 cause the feed pump 105 and the circulation pump 108 to be started (Step S1). The feed pump 105 feeds a gas into the liquid through the gap between the first metal electrode 101 and the insulator 103, thereby causing a bubble 116 to be formed in the liquid 110. Furthermore, the circulation pump 108 causes the liquid 110 to circulate between the reaction tank 106 and the pH treatment tank 107.

The controller 119 also causes the power supply 104 to start applying a power between the pair of electrodes (Step S2). The power generates plasma 115, which causes active species to be produced in the liquid 110. In this step, the timer 117 starts measuring the elapsed time.

While the plasma 115 is generated, the controller 119 measures the hydrogen ion concentration in the liquid by using the pH meter 118 (Step S3) and acquires the time elapsed since the power supply 104 started applying a power between the pair of electrodes (Step S4).

The controller 119 performs a calculation using the hydrogen ion concentration and the elapsed time (Step S5). In Step S5, for example, a product of the hydrogen ion concentration and the elapsed time, or the integral of the hydrogen ion concentration with respect to the elapsed time is calculated. In the example operation illustrated in FIG. 2, an integral is calculated in Step S5. Note that, the concept "integration" herein includes discrete-time integration. For example, in the case where the hydrogen ion concentration is measured a plurality of times during the elapsed time, the product of each of the hydrogen ion concentrations and the time elapsed from the previous measurement to the corresponding measurement is calculated, and the products corresponding to the respective measurements are summed. Alternatively, in the case where the hydrogen ion concentration is measured a plurality of times during the elapsed time at regular interval, the plurality of hydrogen ion concentrations are summed, and the total is multiplied by the length of the interval. By the above calculations, a value corresponding to the above integral can be obtained. Hereinafter, the value corresponding to the above integral which is obtained by performing a summation calculation may be referred to as "integration value".

The controller 119 determines whether the calculated value is larger than the first threshold or not (Step S6). When the calculated value is larger than the first threshold, the controller 119 stops the power supply 104 from applying a power between the pair of the electrodes (Step S7). Otherwise, that is, when the calculated value is not larger than the first threshold, the power supply 104 is allowed to continue applying a power between the pair of electrodes, and a return is made to Step S3.

The first threshold may be set to, for example, $1 \times 10^{-3}$ min·mol/L. In this case, the number of bacteria contained in the liquid 110 to be treated can be reduced by less than 1/100. This makes it possible to estimate whether the liquid 110 to be treated has been sterilized or not.

The magnitude relation between the first threshold and the value (product or integral) based on the hydrogen ion concentration and the elapsed time may be determined by directly comparing the value (product or integral) with the first threshold. Alternatively, another computation substantially equivalent to the comparison between the value (product or integral) and the first threshold may be executed.

After the power supply 104 has been stopped, the controller 119 determines whether the solvent or the solute of the liquid 110 has been changed (Step S8). The term "changed" used herein means that replacement or addition of the liquid 110 has been made. For example, in the case where the liquid treatment apparatus 100 is a washing machine, the "change" of the liquid 110 refers to discharging and charging of water which are performed when finishing the first washing, rinsing, or dewatering and proceeding to the next step. In the case where the liquid treatment apparatus 100 is used as a water purifier for producing drinking water or a tank apparatus included in washing toilet seats, the "change" of the liquid 110 to be treated refers to making up a deficiency of water or adding water.

The controller 119 proceeds to Step S2 when the liquid 110 has been changed ("Yes" in Step S8). When the liquid 110 has not been changed ("No" in Step S8), the feed pump 105 and the circulation pump 108 are stopped (Step S9) and thus the liquid treatment is terminated.

As described above, by the liquid treatment method according to the embodiment, it is possible to automatically determine whether the application of power is to be stopped or continued in accordance with the sterilization ratio. In the case where the first threshold is set so as to correspond to a desired sterilization ratio, it is possible to determine whether generation of the plasma 115 is to be stopped or continued depending on whether the sterilization ratio has reached the desired value or not. Furthermore, it is not required to culture bacteria with effort and time for determining the progress of sterilization.

[3. Experimental Results]

To verify the validity of estimating the sterilization ratio on the basis of hydrogen ion concentration and elapsed time, some experiments were performed as described below.

Figure 3:
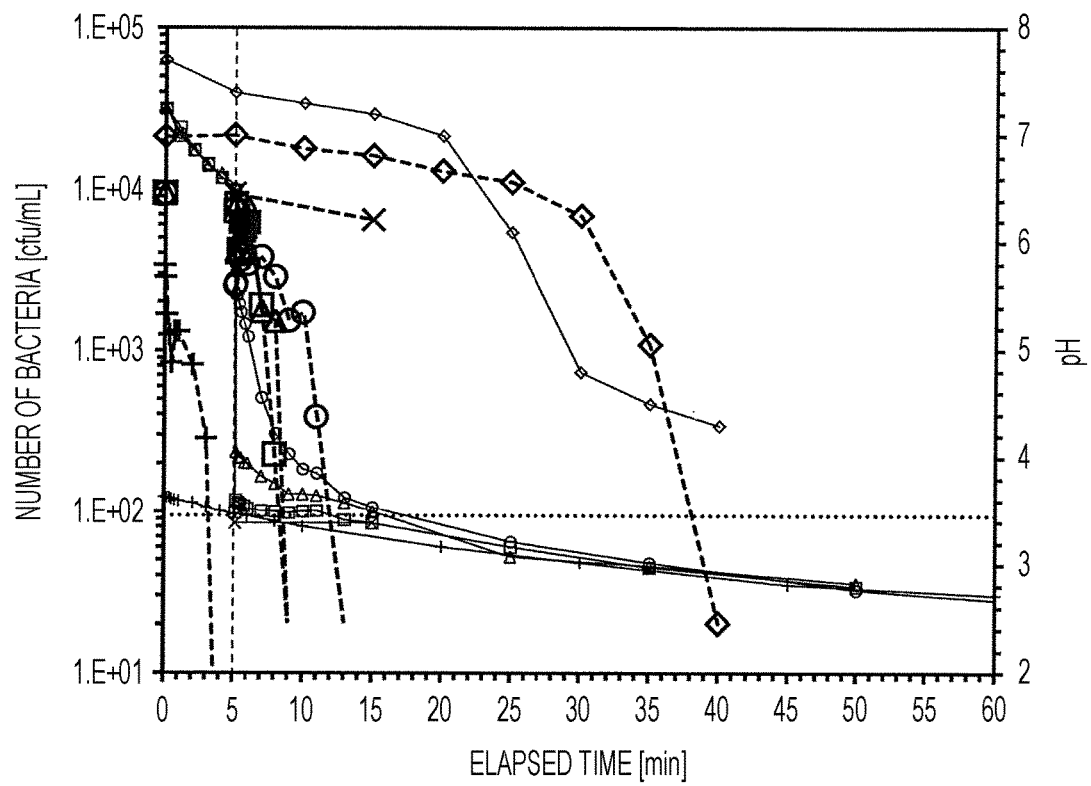
FIG. 3A is a graph illustrating changes in the number of bacteria with the elapsed time and changes in pH with the elapsed time which were determined in Tests 1 to 6.
FIG. 3B is a diagram for explaining Tests 1 to 6 illustrated in FIG. 3A.
Figure 4:
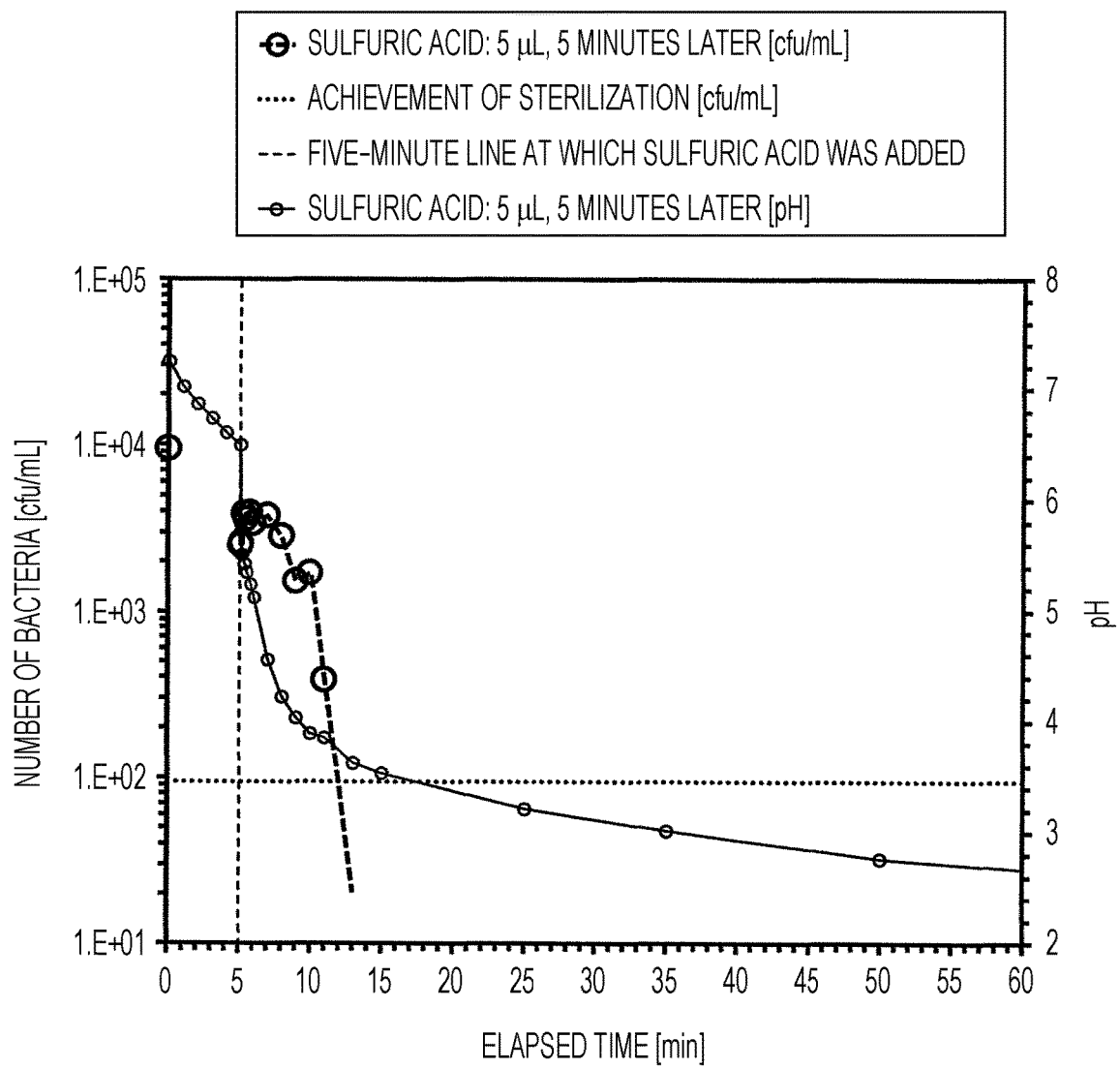
FIG. 4 is a graph illustrating changes in the number of bacteria and pH with the elapsed time which were determined in Test 1.
Figure 5:
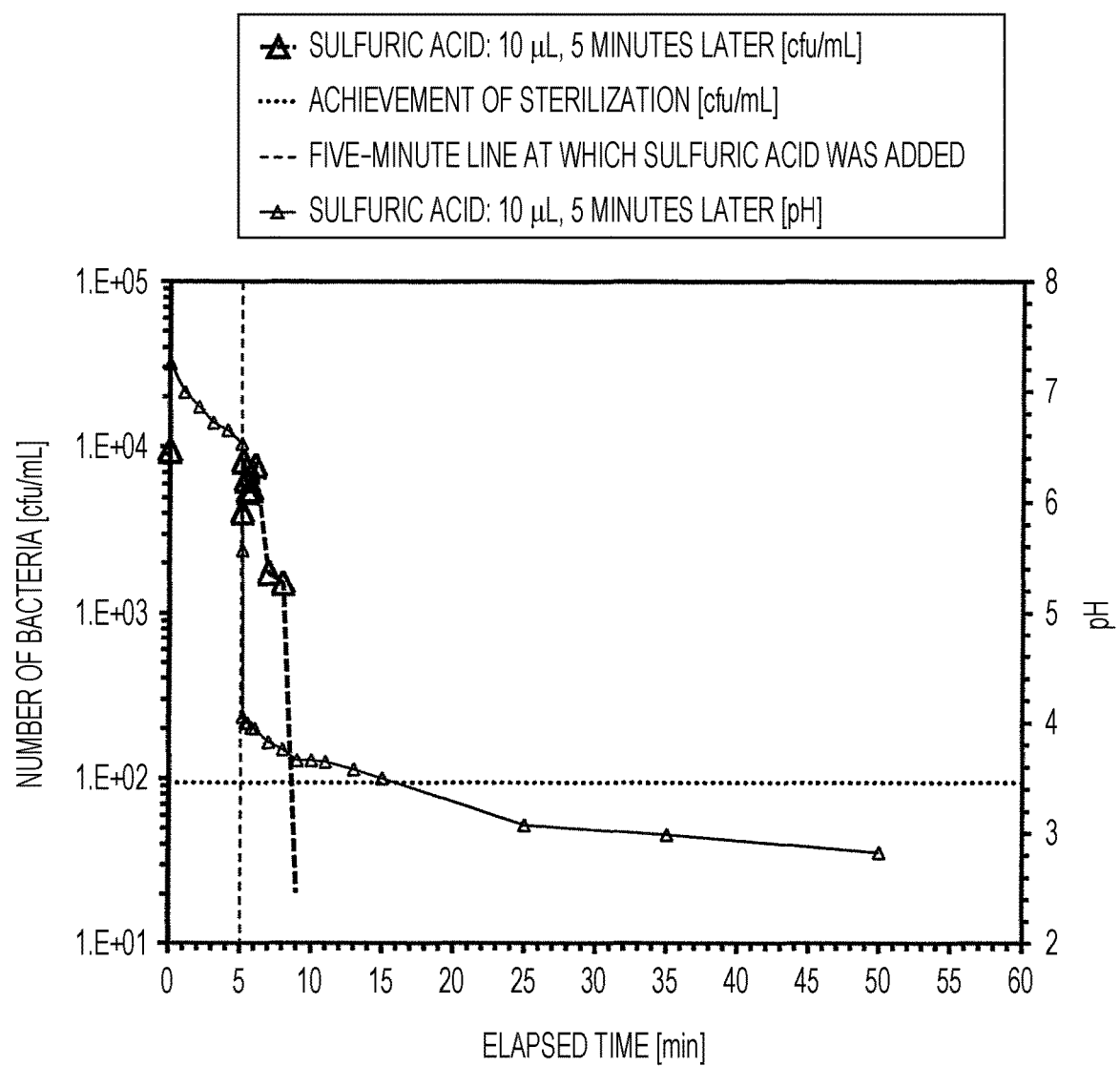
FIG. 5 is a graph illustrating changes in the number of bacteria and pH with the elapsed time which were determined in Test 2.
Figure 6:
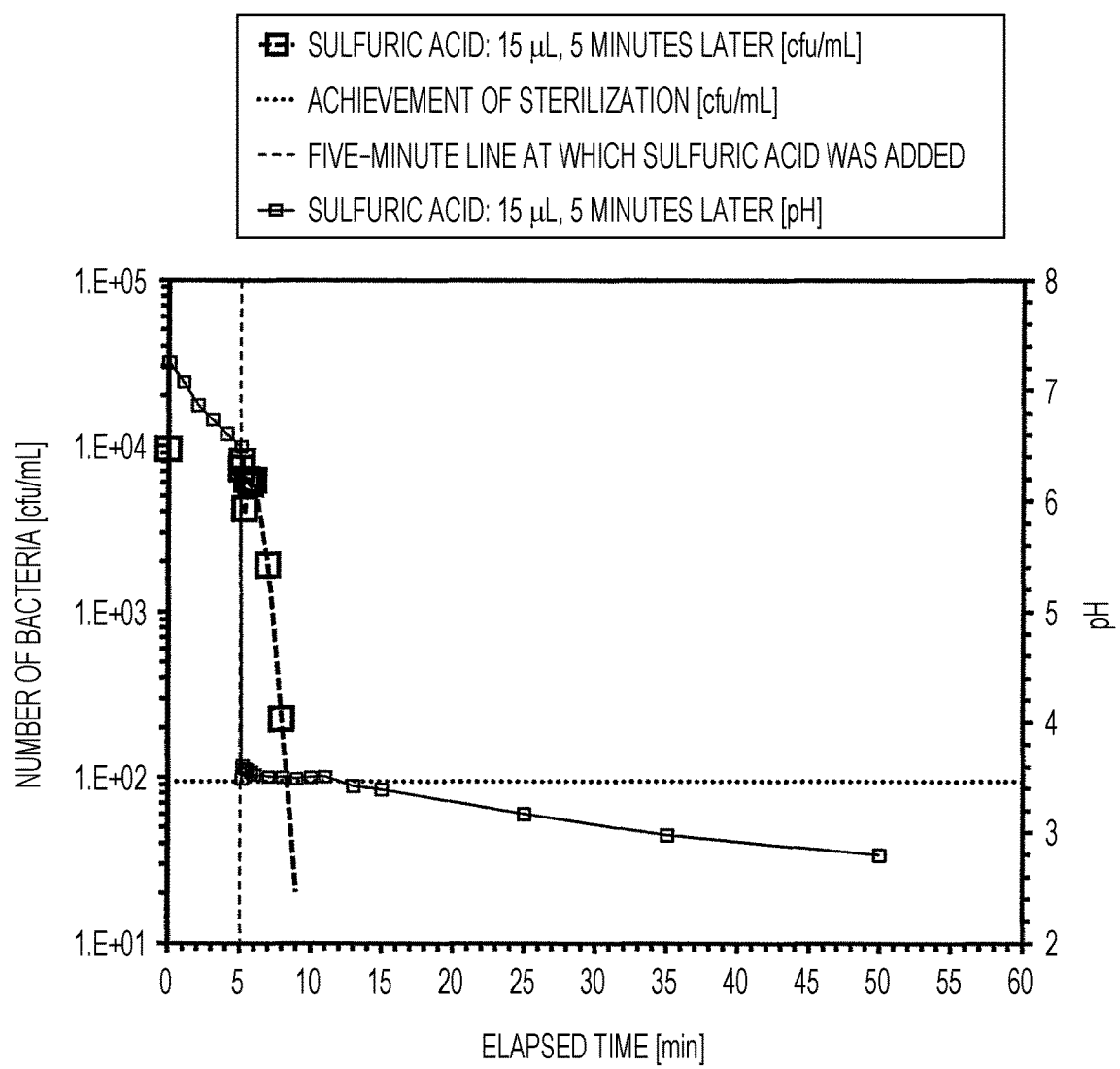
FIG. 6 is a graph illustrating changes in the number of bacteria and pH with the elapsed time which were determined in Test 3.
Figure 7:
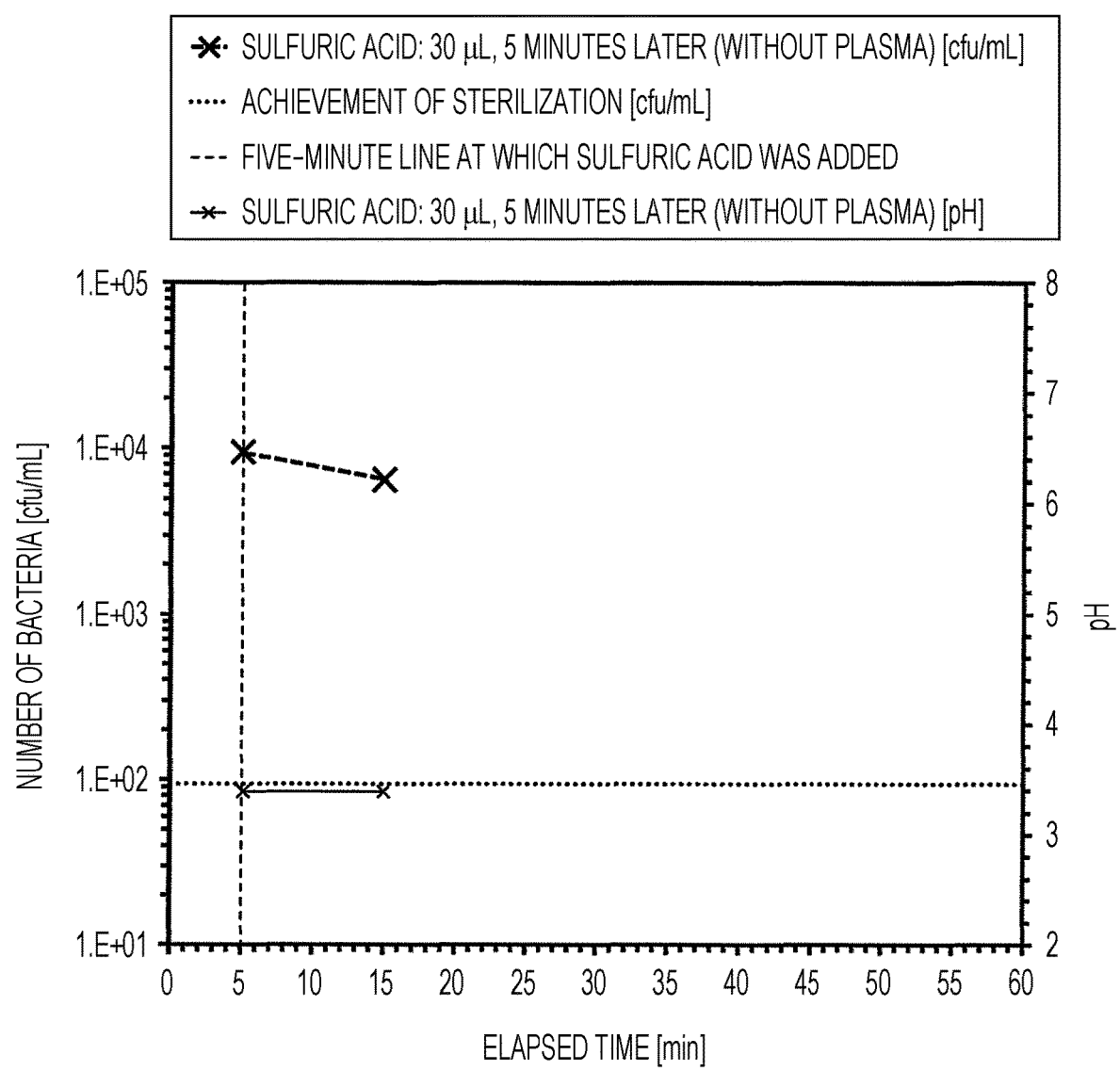
FIG. 7 is a graph illustrating changes in the number of bacteria and pH with the elapsed time which were determined in Test 4.
Figure 8:
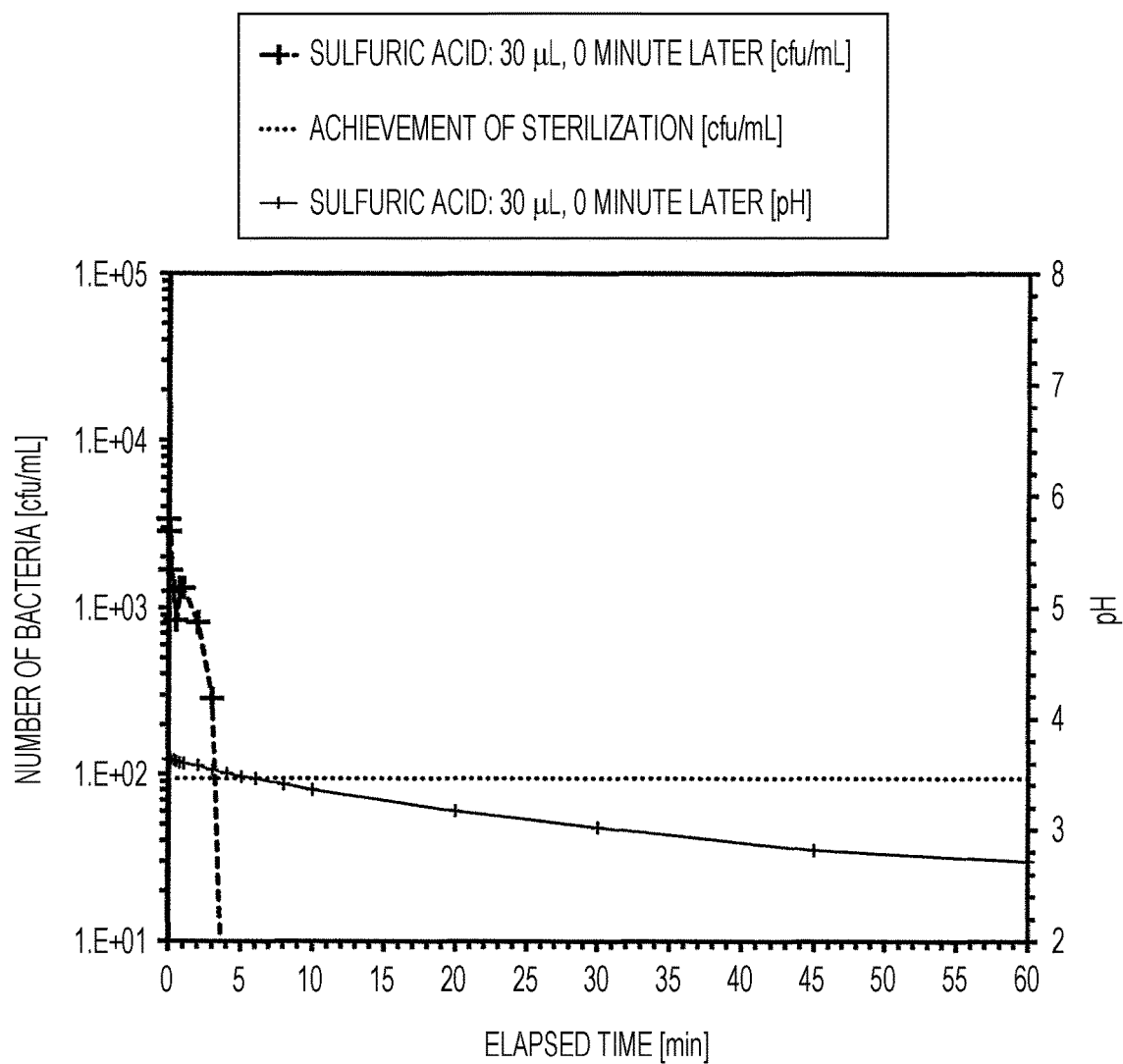
FIG. 8 is a graph illustrating changes in the number of bacteria and pH with the elapsed time which were determined in Test 5.

FIG. 3A is a graph illustrating the changes in the number of bacteria and pH with the elapsed time according to Tests 1 to 6. In FIG. 3A, the horizontal axis denotes the time [min] elapsed since the power supply 104 started application of a power; the vertical axis on the left side denotes the number of bacteria [cfu/ml]; and the vertical axis on the right side denotes pH, that is, hydrogen ion concentration. For example, when the pH of a liquid is 7, the hydrogen ion concentration in the liquid is $1 \times 10^{-7}$ mol/L; when the pH of a liquid is 5, the hydrogen ion concentration in the liquid is $1 \times 10^{-5}$ mol/L. FIG. 3A includes plots of the numbers of bacteria (broken line) and pH values (solid line) which were measured in each of Tests 1 to 6.

Tests 1 to 6 are described below with reference to FIG. 3B. The liquid samples to be sterilized in Tests 1 to 6 were 500 ml of liquids containing bacteria. The initial number of bacteria included in each liquid was about $1 \times 10^4$ cfu/ml or more.

In Test 1, in order to control the pH of the liquid sample, 5 µl of sulfuric acid was added to the liquid sample that was being treated with plasma 5 minutes after the generation of plasma had been started.

In Test 2, in order to control the pH of the liquid sample, 10 µl of sulfuric acid was added to the liquid sample that was being treated with plasma 5 minutes after the generation of plasma had been started.

In Test 3, in order to control the pH of the liquid sample, 15 µl of sulfuric acid was added to the liquid sample that was being treated with plasma 5 minutes after the generation of plasma had been started.

In Test 4, the liquid sample was not treated with plasma and left standing for 5 minutes. Subsequently, 30 µl of sulfuric acid was added to the liquid sample in order to control the pH of the liquid sample.

In Test 5, in order to control the pH of the liquid sample, 30 μl of sulfuric acid was added to the liquid sample at the same time as the generation of plasma was started.

In Test 6, the liquid sample was treated with plasma, but sulfuric acid was not added to the liquid sample.

The dotted line in FIG. 3A which is parallel to the horizontal axis is a line at which sterilization is completed. The broken line in FIG. 3A which is parallel to the vertical axis denotes five minutes after generation of plasma had been started, which corresponds to the timing at which sulfuric acid was added to the liquid samples in Test 1 to 4.

In order to facilitate visualization of FIG. 3A, in which the results of six tests overlap one another, the results of Tests 1 to 6 illustrated in the graph of FIG. 3A are separated into FIGS. 4 to 9, respectively.

The graphs illustrated in FIGS. 3A to 9 confirm that the sterilization efficiency was high when the pH of the liquid sample was low as described below.

Figure 9:
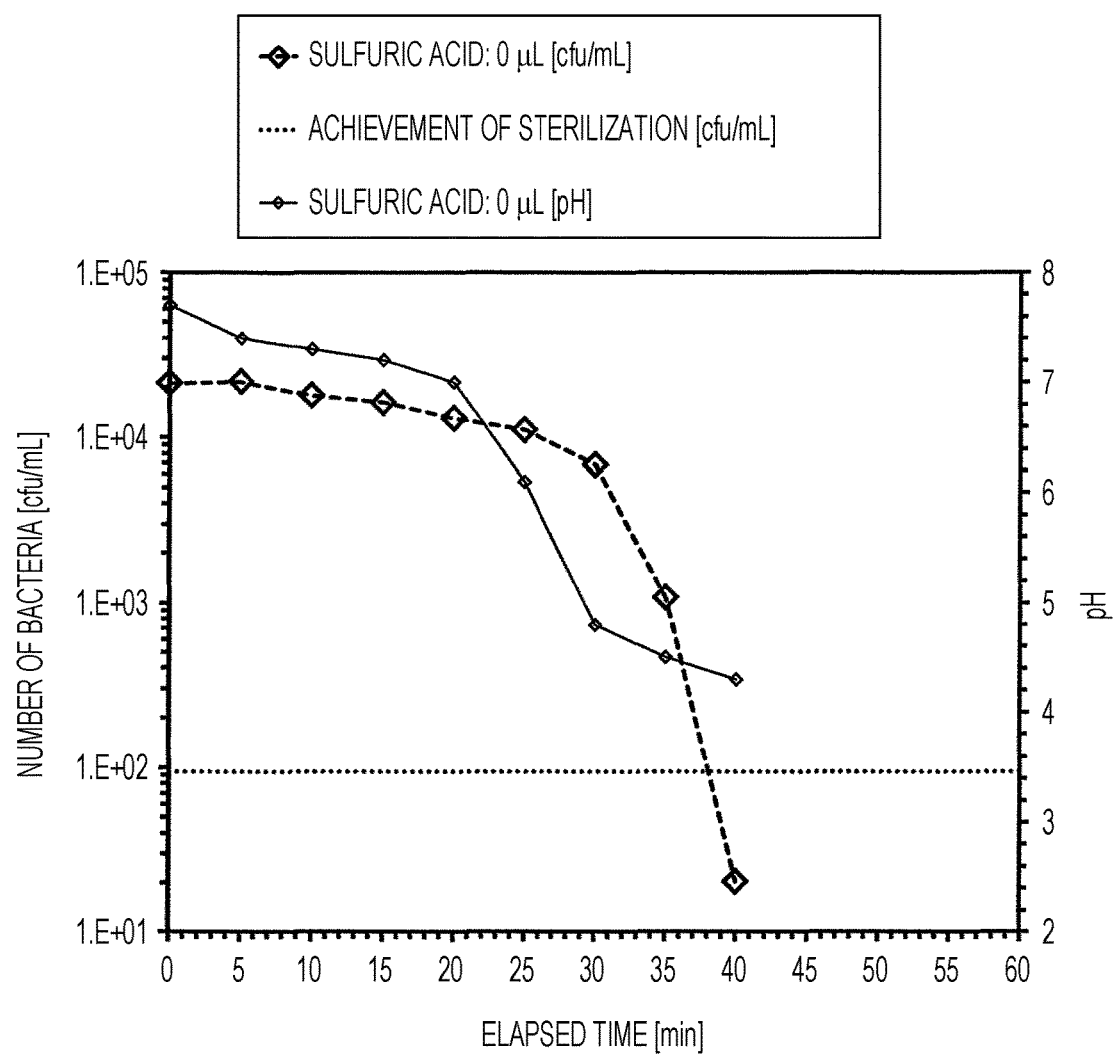
FIG. 9 is a graph illustrating changes in the number of bacteria and pH with the elapsed time which were determined in Test 6.

Sterilization of the liquid samples to which sulfuric acid was added while being treated with plasma (i.e., Tests 1 to 3 and 5; FIGS. 4 to 6 and 8) was completed in a markedly shorter time than sterilization of the liquid samples which were treated with plasma but to which sulfuric acid was not added (i.e., Test 6; FIG. 9). Specifically, in Test 6 illustrated in FIG. 9, the time elapsed from the time the plasma treatment was started to the time the sterilization was completed was about 36 minutes. On the other hand, in Tests 1 to 3 and 5 illustrated in FIGS. 4 to 6 and 8, the time elapsed from the time the plasma treatment was started to the time the sterilization was completed was about 3 to 13 minutes, and the time elapsed from the time the sulfuric acid was added to the time the sterilization was completed was about 3 to 8 minutes.

These results confirm that, by treating a liquid with plasma after reducing the pH of the liquid to 7 or less, the time required to sterilize the liquid can be markedly reduced by about one tenth at maximum compared with the case where the liquid was treated with plasma without controlling the pH of the liquid.

The relationship between the integral of the hydrogen ion concentration in a liquid with respect to the elapsed time and the number of bacteria contained in the liquid were experimentally confirmed as described below.

Figure 10:
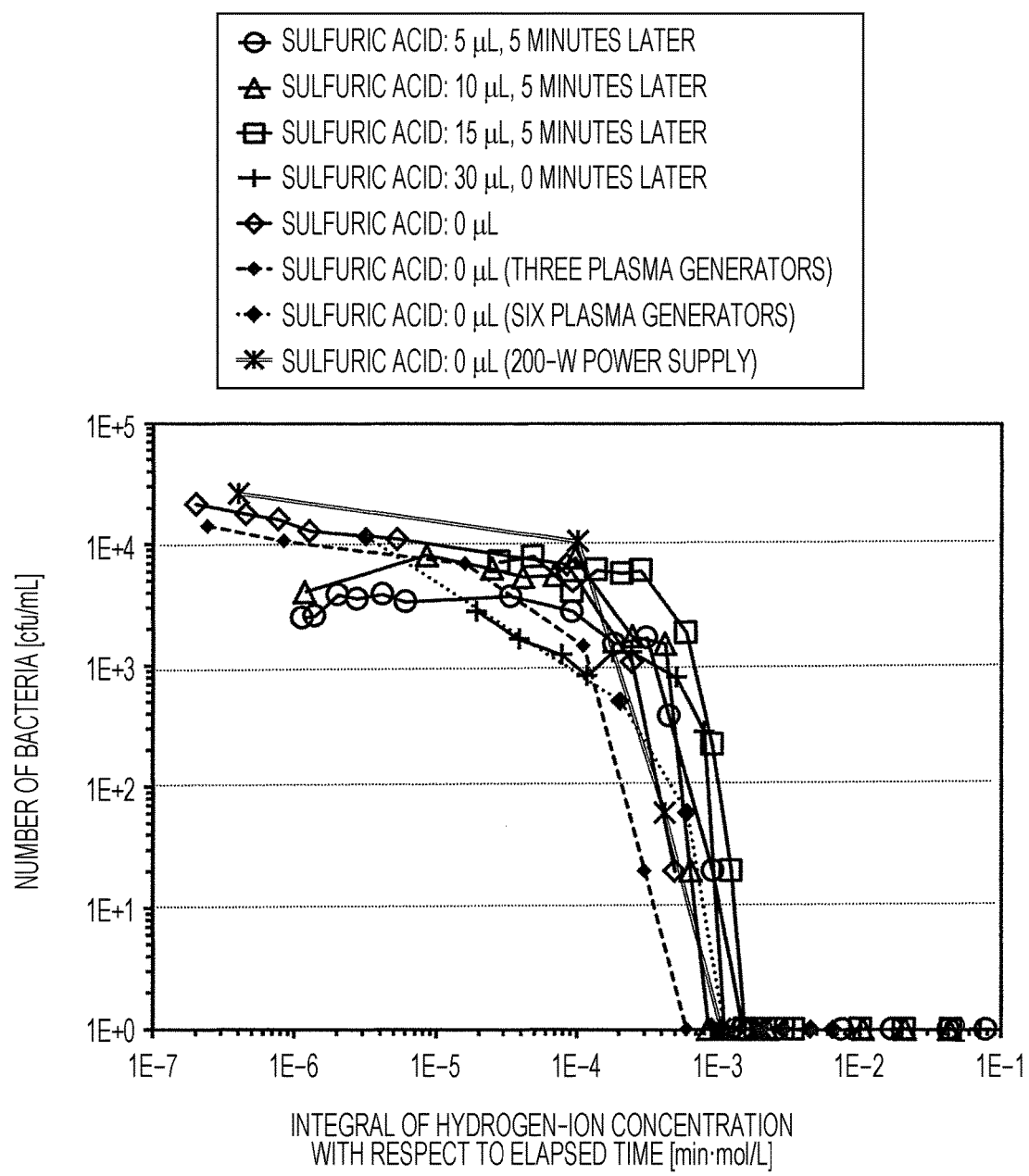
FIG. 10 is a graph illustrating the relationships between the integral of the hydrogen ion concentration with respect to the elapsed time and the number of bacteria which were determined from a plurality of tests.

FIG. 10 is a graph illustrating the relationships between the integral of the hydrogen ion concentration in a liquid with respect to the elapsed time and the number of bacteria contained in the liquid which were determined from the results of the plurality of tests. In FIG. 10, the horizontal axis denotes the integral of the hydrogen ion concentration in a liquid with respect to the elapsed time [min·mol/l]; and the vertical axis denotes the number of bacteria contained in the liquid [cfu/ml].

FIG. 10 illustrates the results of Tests 1 to 3, 5, and 6 described above and the results of Tests 7 to 9 described below. In Tests 7 to 9, similarly to the other tests described above, 500 ml of a liquid in which the initial number of bacteria was about $1 \times 10^4$ cfu/ml or more was used as a liquid sample to be sterilized. In Tests 7 to 9, similarly to Test 6, the liquid sample was treated with plasma, but sulfuric acid was not added to the liquid sample.

In Test 7, the liquid sample (500 ml) was treated with a reaction tank 106 including three plasma generators each including a first metal electrode 101, a second metal electrode 102, an insulator 103, a power supply 104, and a feed pump 105. The output of each power supply 104 was 30 W.

In Test 8, the liquid sample (500 ml) was treated with a reaction tank 106 including six plasma generators. The output of each power supply 104 was 30 W.

In Test 9, the plasma treatment was performed using a power supply having an output of 200 W instead of the power supply 104 (output: 30 W) used in Test 6.

The results illustrated in FIG. 10 all have tendencies similar to one another, regardless of the amount of sulfuric acid added (or, a reduction in pH due to addition of the sulfuric acid), the amount of the plasma 115 generated, and the amount of power applied. These results confirm that, when the integral of the hydrogen ion concentration in a liquid with respect to the elapsed time is known, the approximate proportion of bacteria remaining in the liquid (or, sterilization ratio) can be estimated.

For example, when the integral of the hydrogen ion concentration in a liquid with respect to the elapsed time is $1.0 \times 10^{-3}$ min·mol/L or more, it is considered that a sterilization ratio corresponding to a double-digit reduction in the number of bacteria contained in the liquid (e.g., a sterilization ratio such that the number of bacteria contained in the liquid decreases from, for example, $1 \times 10^4$ to $1 \times 10^2$ cfu/ml) has been achieved.

When the integral of the hydrogen ion concentration in a liquid with respect to the elapsed time is $1.1 \times 10^{-3}$ min·mol/L or more, it is considered that a sterilization ratio corresponding to a triple-digit reduction in the number of bacteria contained in the liquid (e.g., a sterilization ratio such that the number of bacteria contained in the liquid decreases from, for example, $1 \times 10^4$ to $1 \times 10^1$ cfu/ml) has been achieved.

When the integral of the hydrogen ion concentration in a liquid with respect to the elapsed time is $1.1 \times 10^{-4}$ min·mol/L or more, it is considered that a sterilization ratio corresponding to a single-digit reduction in the number of bacteria contained in the liquid (e.g., a sterilization ratio such that the number of bacteria contained in the liquid decreases from, for example, $1 \times 10^4$ to $1 \times 10^3$ cfu/ml) has been achieved.

Thus, it is considered that the sterilization ratio can be estimated on the basis of the integral of the hydrogen ion concentration in a liquid with respect to the time elapsed since discharge of plasma was started.

The sterilization ratio may alternatively be estimated using the product of the hydrogen ion concentration and the elapsed time instead of the integral of the hydrogen ion concentration with respect to the elapsed time. However, it is considered that the sterilization ratio can be estimated with higher accuracy by using the time integral than by using the above product.

The time elapsed since discharge of plasma was started is considered to be the same as the time elapsed since active species was brought into contact with the liquid to be sterilized. Therefore, it is considered that an effect similar to the effect confirmed by the above-described test results may be achieved by a method in which, for example, a liquid is sterilized by being mixed with a liquid containing active species.

Modification

A liquid treatment method according to a modification of the embodiment is described below.

Figure 11:
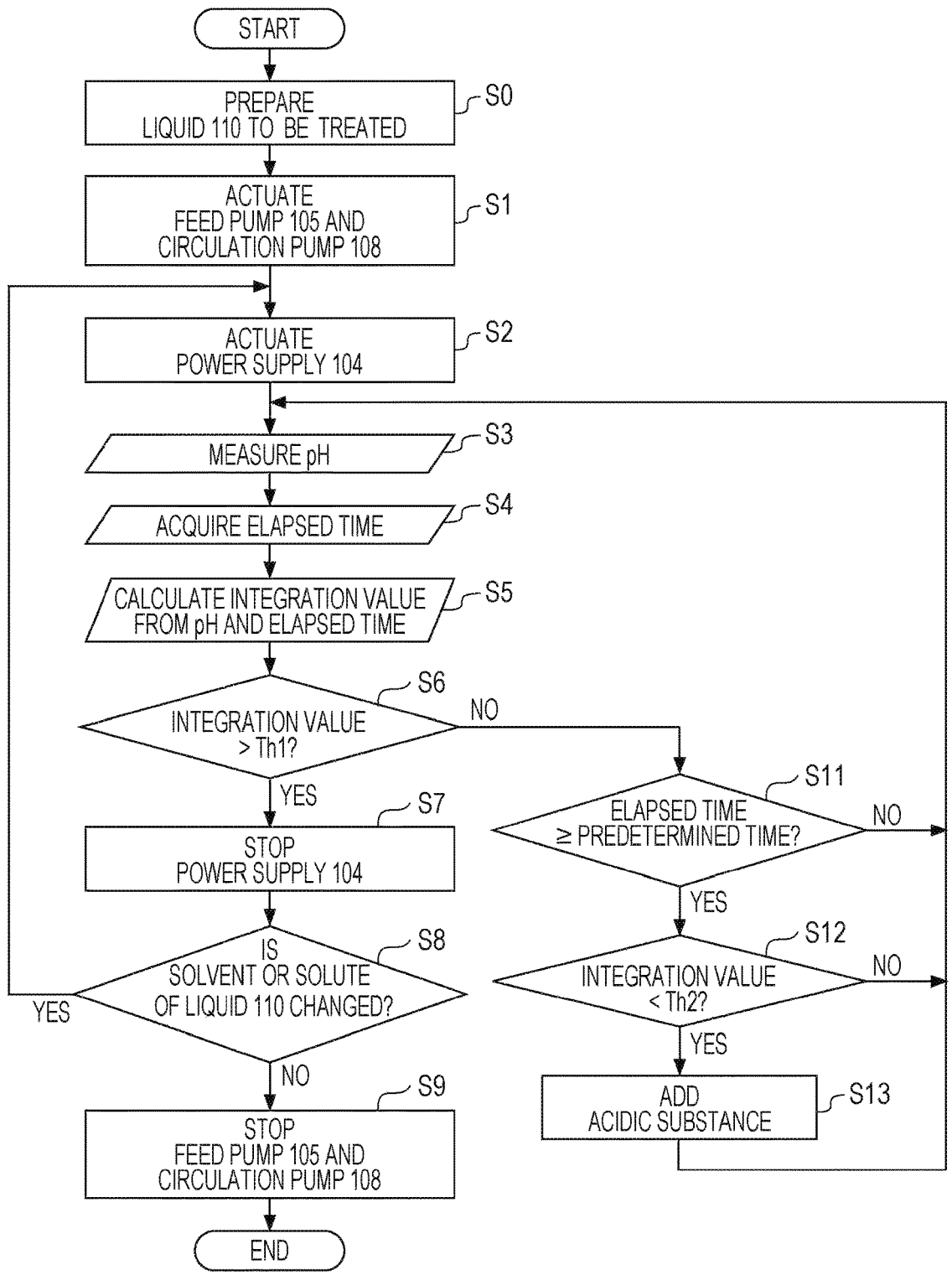
FIG. 11 is a flowchart illustrating an example of a liquid treatment method according to a modification of an embodiment.

FIG. 11 is a flowchart illustrating the liquid treatment method according to the modification of the embodiment. The flowchart illustrated in FIG. 11 differs from that illustrated in FIG. 2 in that Steps S11 to S13 are performed while a return is made from Step S6 to Step S3. The flowchart illustrated in FIG. 11 is described below with particular emphasis on the difference from the method described in FIG. 2.

The controller 119 proceeds to Step S11 when the integration value is not larger than the first threshold in Step S6 ("No" in Step S6). In Step S11, whether the elapsed time has reached a predetermined time is determined. When the elapsed time is less than the predetermined time ("No" in Step S11), a return is made to Step S6. When the elapsed time is equal to or more than the predetermined time ("Yes" in Step S11), the process proceeds to Step S12. In Step S12, whether the integration value is smaller than a second threshold or not is determined. When the integration value is smaller than the second threshold ("Yes" in Step S12), an acidic substance is added to the liquid 110 (Step S13) and a return is made to Step S6. Otherwise, that is, when the integration value is equal to or larger than the second threshold ("No" in Step S12), a return is made to Step S6. The second threshold is equal to or smaller than the first threshold.

In this method, when the sterilization effect is smaller than the expected one at the time a predetermined amount of time has elapsed, the pH of the liquid is reduced by adding an acidic substance to the liquid. This increases the sterilization effect and consequently reduces the time required for sterilization.

The second threshold may be equal to or smaller than the first threshold. The predetermined time set in Step S11 may be the time at which the above-described integration value is empirically considered to reach the second threshold.

The acidic substance may be an acidic chemical or an acidic chemical solution. For example, in the case where the liquid treatment apparatus 100 is used as a washing machine, the acidic substance used in Step S13 may be an acidic detergent. Alternatively, the liquid treatment apparatus 100 may include an electrolyzer that promotes the acidification of the liquid to be treated.

In the above-described embodiments, the steps of the liquid treatment method may be each achieved by using an exclusive hardware or by executing a software program appropriate for the component. The steps of the liquid treatment method may each achieved by a processor such as a CPU loading and executing a software program stored in a recording medium such as a hard disk or a semiconductor memory.

In other words, this program causes a computer to execute the liquid treatment method illustrated in FIG. 2 or 11.

Various alternations, replacement, addition, and omission may be done in the above-described embodiments within the scope of the claims attached below and the equivalent thereof.

In the present disclosure, the term "liquid to be treated" refers to a liquid that is to be treated with plasma, and the term "liquid to be sterilized" refers to a liquid containing bacteria. The liquid containing bacteria may be directly treated with plasma or may be mixed with another liquid that has been treated with plasma. In other words, the liquid to be treated and the liquid to be sterilized may be identical to or different from each other.

For example, a liquid treatment method according to another embodiment of the present disclosure includes preparing a first liquid; starting to apply a power between a pair of electrodes in order to generate plasma, and thereby producing active species in the first liquid; mixing the first liquid with a liquid to be sterilized so as to produce a second liquid while the plasma is generated; measuring the hydrogen ion concentration in the second liquid; measuring the time elapsed since the first liquid was mixed with the liquid to be sterilized; and stopping application of the power when a value calculated by (a) multiplying the hydrogen ion concentration by the elapsed time or (b) integrating the hydrogen ion concentration with respect to the elapsed time is larger than a first threshold, and continuing the application of the power when the value is equal to or smaller than the first threshold.

For example, a liquid treatment method according to another embodiment of the present disclosure includes preparing a liquid to be sterilized; starting to apply a power between a pair of electrodes in order to generate plasma, and thereby producing active species in the liquid; adding an acidic substance to the liquid while the plasma is generated; measuring the hydrogen ion concentration in the liquid while the plasma is generated; measuring the time elapsed since the acidic substance was added to the liquid; stopping application of the power when a value calculated by (a) multiplying the hydrogen ion concentration by the elapsed time or (b) integrating the hydrogen ion concentration with respect to the elapsed time is larger than a first threshold, and continuing the application of the power when the value is equal to or smaller than the first threshold.

For example, a liquid treatment apparatus according to an embodiment of the present disclosure includes:

a plasma generation device including a pair of electrodes and a power supply that applies a power between the pair of electrodes, the plasma generation device applying a power between the pair of electrodes with the power supply in order to generate plasma and thereby producing active species in a liquid;

a sensor that measures the hydrogen ion concentration in the liquid while the plasma generation device generates plasma;

a timer that measures the time elapsed since the power supply started application of the power; and a controller that stops the power supply from applying the power between the pair of electrodes when a value calculated by (a) multiplying the hydrogen ion concentration by the elapsed time or (b) integrating the hydrogen ion concentration with respect to the elapsed time is larger than a first threshold.

For example, a washing machine according to an embodiment of the present disclosure includes the above-described liquid treatment apparatus.

The liquid treatment method according to the embodiment may be applied to a liquid treatment apparatus including a plasma generation device. Such a device may be used as a sterilization device for producing drinking water, a washing machine, and a tank apparatus included in washing toilet seats, for example.

What is claimed is:

1. A liquid treatment method comprising:
    starting application of a power between a pair of electrodes positioned in a liquid to generate plasma, which causes active species to be produced in the liquid;
    measuring a hydrogen ion concentration in the liquid while the plasma is generated;
    measuring a time elapsed after the starting the application of the power; and
    stopping the application of the power when a value, calculated by (a) multiplying the hydrogen ion concentration by the elapsed time or (b) integrating the hydrogen ion concentration with respect to the elapsed time, is larger than a first threshold.

2. The liquid treatment method according to claim 1, further comprising:

adding an acidic substance to the liquid when the value is smaller than a second threshold at a predetermined time, the second threshold being equal to or smaller than the first threshold.

3. A liquid treatment method comprising:

starting application of a power between a pair of electrodes positioned in a liquid to generate plasma, which causes active species to be produced in the liquid;

mixing the first liquid with a liquid to be sterilized to produce a second liquid while the plasma is generated;

measuring a hydrogen ion concentration in the second liquid;

measuring a time elapsed after the mixing the first liquid with the liquid to be sterilized; and stopping the application of the power when a value, calculated by (a) multiplying the hydrogen ion concentration by the elapsed time or (b) integrating the hydrogen ion concentration with respect to the elapsed time, is larger than a first threshold.

4. A liquid treatment method comprising:

starting application of a power between a pair of electrodes positioned in a liquid to generate plasma, which causes active species to be produced in the liquid;

adding an acidic substance to the liquid while the plasma is generated;

measuring a hydrogen ion concentration in the liquid while the plasma is generated;

measuring a time elapsed after the adding the acidic substance to the liquid; and stopping the application of the power when a value, calculated by (a) multiplying the hydrogen ion concentration by the elapsed time or (b) integrating the hydrogen ion concentration with respect to the elapsed time, is larger than a first threshold.

* * * * *